United States Patent [19]

Mueller et al.

[11] 4,442,306

[45] Apr. 10, 1984

[54] PRODUCTION OF TERTIARY AMINES

[75] Inventors: Herbert Mueller, Frankenthal; Hartmut Axel, Schwetzingen; Arnold Wittwer, Ludwigshafen, all of Fed. Rep. of Germany

[73] Assignee: BASF Aktiengesellschaft, Fed. Rep. of Germany

[21] Appl. No.: 400,133

[22] Filed: Jul. 20, 1982

[30] Foreign Application Priority Data

Jul. 22, 1981 [DE] Fed. Rep. of Germany ....... 3128889

[51] Int. Cl.³ ............................................. C07C 85/06
[52] U.S. Cl. .................................................. 564/479
[58] Field of Search ........................................ 564/479

[56] References Cited

U.S. PATENT DOCUMENTS

| | | | |
|---|---|---|---|
| 2,412,209 | 12/1946 | Dickey et al. | 564/479 X |
| 2,609,394 | 9/1952 | Davies et al. | 564/479 |
| 2,795,600 | 6/1957 | Chitwood et al. | 564/479 X |
| 3,223,734 | 12/1965 | Fallstad et al. | 260/583 |
| 3,708,539 | 1/1973 | Fenton | 260/585 B |
| 4,145,307 | 3/1979 | Krapf et al. | 564/479 UX |

FOREIGN PATENT DOCUMENTS 2907869 of 0000 Fed. Rep. of Germany .
3005953 of 0000 Fed. Rep. of Germany .
2625196 of 0000 Fed. Rep. of Germany .

OTHER PUBLICATIONS

Russian Chemical Reviews 34, (1965), pp. 843–853.
L. Spialter, J. A. Pappalardo, "The Acyclic Aliphatic Tertiary Amines", The Macmillan Company, New York, (1965) (Cover Pages Only).

*Primary Examiner*—Paul F. Shaver
*Attorney, Agent, or Firm*—Keil & Witherspoon

[57] ABSTRACT

Tertiary amines are produced by reacting a secondary amine having identical or different substituents, in particular a readily volatile amine, with a primary or secondary monohydric or polyhydric alcohol, in particular a sparingly volatile fatty alcohol, over a copper catalyst formed directly from copper formate under the reaction conditions.

8 Claims, No Drawings

PRODUCTION OF TERTIARY AMINES

The catalytic alkylation of ammonia or an amine with an alcohol is known. The catalysts used in this reaction are either dehydrating oxides, for example those of aluminum, thorium, tungsten and chromium, or hydrogenation or dehydrogenation catalysts containing the active metals copper, nickel and cobalt or noble metals. The hydrogenation/dehydrogenation catalysts are solids, and are employed as suspensions when present in powder form, or as moldings in a fixed bed catalyst. Liquid-phase and gas-phase processes have been proposed. A detailed description of the field is given by V. A. Nekrasova and N. I. Shuikin in Russian Chemicals Review, 34 (1965), 843, and in "The acyclic aliphatic tertiary amines" by L. Spialter and J. A. Pappalardo, the Macmillan Company, 1965. The preparation of tertiary amines by alkylation of a secondary amine with an alcohol is particularly difficult. As a result of transalkylation reactions, secondary and primary amines are obtained as by-products, which are difficult to separate off from the desired tertiary amine, and may be troublesome when the latter is used.

In order to be able to obtain tertiary amines in high yields, German Laid-Open Application DOS No. 1,493,781 has therefore proposed reacting not less than the stoichiometric amount of a secondary amine with an alcohol, since an excess of alcohol is said to be disadvantageous. Although it appears that this measure produces a certain improvement in the selectivity of the amine in the reaction with a secondary alcohol, the degree of conversion of the amine is low. In the case of primary alcohols, only small conversions and poor selectivities are achieved, since the residues formed as by-products reduce the yields.

U.S. Pat. No. 3,708,539 describes an improved process for the preparation of tertiary amines, in which an alcohol is reacted, in the liquid phase, with a secondary amine over a ruthenium, osmium, rhenium or technetium catalyst. A particular disadvantage of this process is the fact that the conversion and yield, based on the alcohol employed, are insufficient, in relation to the value of the catalyst raw materials, for an industrial process.

According to U.S. Pat. No. 3,223,734, Raney nickel, copper/chromium oxide, palladium on charcoal, or nickel on diatomaceous earth may be used as the catalyst for the preparation of tertiary amines. However, as the Examples of the above patent show, even these catalysts do not give advantageous results, and, in addition, uneconomically large amounts are frequently required.

Japanese Preliminary Published Application No. 19,604/77 describes a substantially improved method for the preparation of dimethyldodecylamine, in which a yield of about 90% is obtained using a copper/chromium oxide catalyst on diatomaceous earth.

The catalysts mentioned in the above patent publications are solid (heterogenous) catalysts with a relatively low specific activity. It is therefore necessary to employ large amounts of catalyst, for example from 2 to 10%, based on the reaction mixture. Although solids have the advantage that they can readily be separated off from the substrate, after the reaction, by filtration or sedimentation, there are, however, still substantial technical and economic problems to be overcome. At a catalyst concentration of above 5%, problems of mixing occur, for example, in processes carried out in suspension. In addition, the elimination or working up of the catalysts which have been contaminated by organic constituents and have become inactive are especially demanding when these catalysts are supported catalysts, or when they require toxic constituents (chromates) for their preparation. Moreover, the selectivities of these catalysts are also not completely satisfactory.

German Laid-Open Applications DOS No. 2,907,869 and DOS No. 3,005,953 have therefore proposed a pseudo-homogeneous, colloidal catalyst system which does not possess the above disadvantages of the solid catalysts. These colloidal catalysts are formed when a mixture of copper carboxylate or silver carboxylate with carboxylates of elements of group VIII of the periodic table (including manganese and zinc) and alkali metal and alkaline earth metal carboxylates is reduced with hydrogen or an aluminum-alkyl compound. Instead of carboxylates, it is possible to use inner complexes of, for example, dicarbonyl compounds.

As is generally the case in aminolyses, these catalysts possess high activity and selectivity only when a combination of several active metals in the correct ratio is used. A further disadvantage is that the catalysts have to be activated, before the actual reaction, by reduction with hydrogen or an aluminum-alkyl. Finally, the catalysts cannot be separated off mechanically from the product in a simple manner, but must be separated off by distillation. The catalyst thus remains in the high-boiling or non-distillable residues formed at the same time. Although the catalysts can be directly employed for a further reaction, this procedure inevitably produces a progressive increase in the level of by-products in the reaction system. Apart from the fact that sensitive substances may not remain unaffected in the presence of catalytic metals during distillation, and may undergo changes, there still remains the problem of separating off these catalysts from the residues at a later time, in a manner which does not cause pollution.

It is an object of the present invention to produce aliphatic or cycloaliphatic tertiary amines in such a manner that a high yield of the desired product with a very low content of primary and secondary amines is obtained using a minimal amount of catalyst. Moreover, conversion of the alcohol should be nearly as complete as possible, since it is often difficult to separate it off later from the desired product. The boiling points of the alcohol and of the corresponding amine are so close together, in particular in the case of the high molecular weight fatty amines, that they cannot be separated by distillation. The nature of the catalyst after the reaction should be such that it can readily be separated off quantitatively from the product and used for further reactions. Finally, residues, high molecular weight condensates and side reactions should be substantially excluded. The catalyst for a reaction of this type must moreover be a simple, readily obtainable, cheap chemical which is directly active for the reaction, without itself requiring an activating step.

We have found that this object is achieved, and that symmetrical or asymmetrical tertiary amines of not more than about 40 carbon atoms in total are advantageously obtained, by reacting a secondary amine having identical or different substituents with a primary or secondary monohydric or polyhydric alcohol, in particular an alcohol which is of 6 or more carbon atoms and has the characteristics of a fatty alcohol, over a copper catalyst, in the presence or absence of hydrogen, when the catalyst used is formed directly from copper formate under the reaction conditions.

The process is advantageously carried out in a conventional manner, by feeding the particular amine, at the rate at which it reacts, into the liquid reaction mixture containing the particular alcohol, and removing water at the rate at which it is formed.

The object is thus most advantageously achieved by combining the alcohol with the amine in the presence of a small amount of copper formate, so that very much less than the stoichiometric amount of amine is present, and the alcohol essentially forms the liquid phase. The liquid phase therefore contains the alcohol, which is present in high molar excess at least at the beginning of the reaction. At any particular time, the reaction mixture should not contain more than, for example, 10% by weight of the amine. Under these conditions, the catalyst develops a maximum catalytic action without additional activation beforehand.

The process is most simply carried out by introducing the amine to be converted, in vapor form, into the liquid reaction mixture, which at the beginning of the reaction contains a small amount of amine (not more than 3% by weight), the copper formate and the alcohol. When, in general, about 150° C. is reached, the intended reaction begins without further measures being required.

The amine to be converted may be added in liquid form, for example via a metering device, this method being suitable when the reaction temperature is above the boiling point of the amine, and the reaction is carried out isobarically. In this manner, also, the accumulation of relatively large or even excess amounts of amine may be avoided.

According to the above description, when a batch-wise process is employed, the reaction is carried out, with gradual addition of the amine in each case, until the alcohol has been consumed, and the desired amine can be obtained from the liquid reaction mixture by distillation.

In a corresponding modification employing a continuous procedure, the amine to be converted is fed, for example in gaseous form, counter-current to the liquid reaction mixture containing the alcohol and the suspended catalyst, with or without the tertiary amine. If necessary, a zone for further reaction should be provided in this procedure.

An important measure for obtaining optimum results comprises removing the resulting water continuously from the reaction mixture, so that it is advantageous to carry out the reaction under conditions such that water leaves the reaction mixture of its own accord as a gas.

The invention may be appreciated by considering the following: if the reaction takes place in the gas phase, a very high reaction temperature must be chosen, since the alcohols are in general of relatively low volatility; as a result, a low yield and an impure product are obtained. If the reaction is carried out in the liquid phase, using, for example, a high pressure, depending on the temperature, and a high concentration of amine, in the case of a readily volatile amine, such as dimethylamine, the course of the reaction is substantially non-specific. The amount of water, usually increasing with the conversion, also produces this effect.

Advantageously, the reaction conditions described in German Laid-Open Application DOS No. 2,625,196 are maintained. By using copper formate as the catalyst, it is possible in this procedure to manage with substantially smaller amounts of catalyst, to obtain a purer product and to increase the yield further.

Furthermore, it is advantageous to carry out the reaction in the presence of, for example, from 0.1 to 50% by weight, preferably from 1 to 10% by weight (based on the copper catalyst), of a base, such as an alkali metal hydroxide or an alkaline earth metal hydroxide, eg. sodium hydroxide, potassium hydroxide or calcium hydroxide, and particularly advantageous to use the corresponding carbonates; several of the above compounds may be present simultaneously.

The reaction may be carried out in the absence of hydrogen, corresponding to the equation of the overall conversion. Thus, the reaction, for example between an alcohol and dimethylamine, proceeds, merely as a result of introducing dimethylamine gas into the reaction mixture, as soon as the required reaction temperature is reached. The desired amine is obtained in a yield of above 95% at an alcohol conversion of above 99%. However, it has proved advantageous in some cases to feed a small amount of hydrogen into the reaction medium, thereby promoting the activity of the catalyst and preventing the formation of small amounts of unsaturated compounds.

No special requirements are made in respect of the nature and properties of the copper formate. It is possible to employ, without pretreatment, for example commercial copper formate containing water of crystallization, but anhydrous copper formate may be employed with equal success. The manner in which the copper salt has been prepared is of no importance with regard to its catalytic activity. For example, a suitable catalyst is obtained when the formate is prepared from copper oxide, hydroxide, stearate or carbonate and formic acid. This reaction may also be carried out with the copper compound and formic acid in the absence of water, for example in the alcohol intended for the aminolysis. It may be assumed that the actual catalyst is formed directly by the reaction of copper formate with constituents of the reaction mixture. The amount of copper formate required to achieve an adequate conversion is from 0.01 to 2% by weight, preferably from 0.05 to 1% by weight (calculated as metallic copper), based on the starting alcohol. Since, when pure starting materials are used, the catalyst formed from the copper formate is virtually never exhausted and can be re-used, the small cost which it entails is of no significance, and it is also possible to separate it off at some stage, reconvert it into copper formate, and re-use it, if necessary after the addition of a further amount of a basic alkali metal compound or alkaline earth metal compound.

The alcohol used as a starting material may possess a linear or branched, saturated or unsaturated aliphatic hydrocarbon chain which may be interrupted by heteroatoms, in particular oxygen. Although it is also possible to employ a secondary alcohol in the present process, the reaction with a primary alcohol is preferred. The best results are thus obtained using a monofunctional or polyfunctional primary alcohol of 2 or more carbon atoms.

End products which are particularly important industrially are the fatty amines; these are derived from alcohols of about 6 to 22 carbon atoms, ie. fatty alcohols. Examples of such alcohols are octyl alcohol, lauryl alcohol, myristyl alcohol, cetyl alcohol, oleyl alcohol, stearyl alcohol, tridecyl alcohol and pentadecyl alcohol, and mixtures of these compounds, and also dihydric alcohols, such as ethylene glycol, diethylene glycol, butane-1,4-diol and hexane-1,6-diol. Among alcohols of less than about 6 carbon atoms, the sparingly volatile polyhydric alcohols are preferably reacted.

Instead of the alcohols, it is also possible to employ linear or branched, saturated or unsaturated, aliphatic aldehydes, eg. lauryl aldehyde, or oxaldehydes, which are reduced to alcohols in the presence of hydrogen under the reaction conditions.

Secondary amines suitable for the novel process have identical or different aliphatic or cycloaliphatic substituents, each of, for example, 1 to 18 or more, preferably 1 to 16, in particular 1 to 12, carbon atoms. Examples of industrially important secondary amines are dimethylamine, diethylamine, methylethylamine, dipropylamine and dioctylamine.

The reaction takes place in general at from 150° to 250° C., preferably from 190° to 220° C. It may be carried out under atmospheric, superatmospheric or reduced pressure, for example at from 10 mbar to 6 bar, the pressure range chosen depending also on the properties of the reactants and on the reaction temperature chosen.

If a high-boiling alcohol, for example decanol, lauryl alcohol or tridecyl alcohol, is used for the alkylation, it is sufficient to heat the alcohol in the presence of the copper formate, with or without the addition of the activating alkali metal compound, and to introduce the secondary amine at the rate at which it reacts. The water formed in the reaction is distilled off continuously from the reaction system, and this operation can be assisted by using a suitable solvent, for example an aliphatic or aromatic hydrocarbon, to remove the water of reaction as an azeotrope, which is separated off. A suitable reaction space is therefore, for example, a reactor equipped with a stirring apparatus, a condenser and a water separation vessel. A particularly simple method comprises bubbling the amine and, if desired, hydrogen, in the form of a gas, through the alcohol which has been brought to the reaction temperature. The water formed is removed, as a vapor, from the reaction zone and condensed, and the unconsumed gas is recycled. Depending on the reaction temperature and the amount of catalyst, up to 1 mole, preferably from 0.3 to 0.6 mole, of the amine per mole of alcohol per hour may be passed into the reaction mixture. The amount of hydrogen, when it is used, is of the same order of magnitude or lower. In any case, it may be varied within wide limits. It can be seen from the above description that favorable reaction conditions permit the reaction to be completed in about 1-10 hours. Shorter reaction times are not advisable, owing to the amount of heat required to vaporize the water of reaction. On the other hand, longer reaction times can be accepted without incurring any disadvantages for the reaction. The reaction rate is of course always determined by the amount of amine added per unit of time. Normally, this amount is chosen so that the concentration of secondary amine remains constant at a few percent of the reaction mixture.

A particular result of the invention is that the product, after the reaction is complete and the catalyst has been separated off mechanically, is of sufficient purity for most fields of use, without requiring further purification. The products are all colorless, and most of them are contaminated with less than 5% of by-products.

In a large number of cases, for example, the tertiary amines are used not as such but as quaternary salts, after they have been reacted, for example with benzyl chloride or methyl chloride. Although the quality requirements of, for example, dimethyllaurylamine or dimethylmyristylamine are very stringent, the tertiary amines prepared according to the invention can be put to the desired end use without distillation. Since these tertiary amines are very high-boiling compounds, dispensing with purification by distillation results in a significant saving of energy. Compared to the procedure described in German Laid-Open Application DOS No. 2,907,869, not only does the novel process possess the above advantages, but the alkylation therein occurs at a noticeably lower temperature, on average at from 10° to 20° C. lower. This is also an important factor in explaining the high selectivity achieved by the novel process. Since it is inter alia an object of the novel process to convert the alcohol completely, the total amount of amine fed in is not less than the stoichiometric amount. When a readily volatile amine is used, a certain excess towards the end of the reaction may be advantageous. This may be on average from 5 to 100 mole%, preferably from 10 to 30 mole%, ie. the conversion conditions may be maintained until an appropriate conversion can be expected. The amine supplied in excess is then removed. It is important that the amine be added in the course of the reaction at the rate at which it reacts. In accordance with the invention, an excess of alcohol is thus present for virtually the total duration of the reaction, ie. as long as the alcohol is still present in the reaction mixture in a significant concentration. Such reaction conditions are very simple to achieve in a counter-current process, which, moreover, may be carried out continuously.

EXAMPLE 1

1,600 kg of a 70:30 mixture of n-dodecanol and n-tetradecanol, 28.5 kg of copper formate ($Cu(CHO_2)_2.4-H_2O$) and 3 kg of calcium hydroxide are introduced, under atmospheric pressure, into a stirred apparatus, and heated to 200° C. During the heating period (20 minutes) the reaction mixture is kept saturated with hydrogen and dimethylamine. The reaction begins at above 170° C., and an aqueous phase separates out in a distillation head in the form of a water-separating head. Small amounts of the alcohol introduced are entrained, and are recycled to the stirred apparatus via the water-separating head. About 30–35 kg/hour of dimethylamine and 5 $m^3$ (s.t.p.)/hour of hydrogen are then fed, in the form of a gas, into the reaction mixture. About 12–15 kg/hour of water of reaction distill off at the beginning of the reaction and are separated off in the water-separating head as an aqueous phase. Any entrained alcohol is recycled to the reactor. After a reaction time of from 8 to 10 hours, the reaction stops, and no more water separates out. The process is permitted to proceed for a further 2 hours under the same conditions, and the supply of amine is then interrupted. The catalyst is allowed to settle out for 1 hours, and the product is then separated by filtration from residues (about 3% of the material employed) of finely-divided catalyst which has not settled out. The colorless filtrate obtained is worked up by distillation, without rectification. A 70:30 mixture of dimethyllaurylamine and dimethylmyristylamine is obtained in a yield of from 96 to 98% of theory, and with a purity, ie. a content of tertiary amines, of more than 99.5%. The amine mixture boils at from 118° to 145° C. under 5 mbar. The distillation residue comprises from 2 to 3%, based on the weight of alcohol employed, of a semisolid material.

A comparable result is also obtained when calcium hydroxide is replaced by barium hydroxide or potassium carbonate. By using sodium carbonate and sodium bicarbonate, the reaction rate is increased by about 20%, and a yield of about 95% is obtained. The reaction rate is decreased slightly (by about 10–15%) when 0.1 part of potassium hydroxide or 0.3 part of calcium oxide is added instead of the calcium hydroxide.

If the reaction is carried out without the addition of a base, complete conversion of the alcohol is obtained, but only after about 30 hours. Even in this case, however, the yield is still 90–92% of the theory.

While virtually no secondary and primary amines can be detected in the end product when an alkali is present, about 0.2–0.3% of a primary amine and about 0.1%, of a secondary amine of a type other than that which was introduced are formed in the absence of an alkali (transalkylation).

EXAMPLE 2

If, instead of dodecanol/tetradecanol, the straight-chain alcohol octanol, decanol or octadecanol is used in the reaction, the same good result is obtained.

No difference is found when the aldehydes are used instead of the alcohols, ie. when instead of the lauryl alcohol/myristyl alcohol mixture, the aldehydes derived therefrom, ie. lauryl aldehyde and myristyl aldehyde, are employed. 30 Cubic meters (s.t.p.)/hour of hydrogen are fed into the reactor in this case.

EXAMPLE 3

The procedure described above is followed, except that 2,000 kg of a mixture of $C_{13}$ and $C_{15}$ oxoalcohols, obtained by hydroformylation of a Ziegler olefin mixture (about 70% of dodec-1-ene and 30% of tetradec-1-ene), 35.5 kg of copper formate ad 2 kg of calcium hydroxide are introduced, and reacted, at 200° C., with dimethylamine and hydrogen (hydrogen partial pressure: about 100 mbar). The reaction is complete after 24 hours. The mixture is allowed to cool and is filtered, and about 2,040 kg of product are obtained. It is worked up by distillation, giving, as the distillate, 1,885 kg of $C_{13}/C_{15}$-dimethylamine having a boiling point of 130°–154° C./5 mbar and an amine number of 229 mg of KOH/g, in good agreement with the hydroxyl number of 250 mg of KOH/g of the alcohol mixture employed. 155 kg of a high-boiling amine mixture remain as the residue.

We claim:

1. A process for the preparation of a symmetrical or asymmetrical tertiary amine of not more than about 40 carbon atoms in total which comprises reacting a secondary amine having identical or different substituents with a primary or secondary monohydric or polyhydric alcohol having 6 or more carbon atoms and having the characteristics of a fatty alcohol, over a copper catalyst, at from 150° to 250° C., in the presence or absence of hydrogen, wherein the catalyst used is formed directly from copper formate under the reaction conditions.

2. The process of claim 1, wherein the reaction is carried out in the presence of a basic alkali metal compound or alkaline earth metal compound.

3. The process of claim 1, wherein the secondary amine is fed, at the rate at which it reacts, into the liquid, alcohol-containing reaction mixture, and water is removed at the rate at which it is formed.

4. The process of claim 1, wherein a readily volatile secondary amine is fed in in vapor form.

5. The process of claim 1, wherein the secondary amine is fed into the reaction mixture at above its boiling point, and the reaction is carried out under a constant pressure.

6. The process of claim 1, wherein, in a batchwise procedure, the reaction is carried out until the alcohol is consumed, and the amine is obtained from the liquid reaction mixture by distillation.

7. The process of claim 1, wherein, in a continuous procedure, a readily volatile secondary amine, in the form of a gas, is fed counter-current to the liquid reaction mixture which contains the alcohol and may or may not contain a tertiary amine, and a region for further reaction may be provided.

8. The process of claim 1, wherein the catalyst which has been separated off from the product is reused for further reactions, if necessary after the addition of a further amount of a basic alkali metal compound or alkaline earth metal compound.

* * * * *